United States Patent [19]

Winter et al.

[11] Patent Number: 5,912,345
[45] Date of Patent: Jun. 15, 1999

[54] PROCESS FOR THE PREPARATION OF LAMOTRIGINE

[75] Inventors: Raymond Geoffrey Winter, Dartford; David Alan Sawyer, Beckenham; Andrew Germain, Greenford, all of United Kingdom

[73] Assignee: Glaxo Wellcome Inc., Research Triangle Park, N.C.

[21] Appl. No.: 08/836,153

[22] PCT Filed: Dec. 29, 1995

[86] PCT No.: PCT/GB95/03048

§ 371 Date: Jun. 25, 1997

§ 102(e) Date: Jun. 25, 1997

[87] PCT Pub. No.: WO96/20934

PCT Pub. Date: Jul. 11, 1996

[30] Foreign Application Priority Data

Dec. 30, 1994 [GB] United Kingdom .................. 9426439
Dec. 30, 1994 [GB] United Kingdom .................. 9426447

[51] Int. Cl.⁶ ................................................ C07D 253/06
[52] U.S. Cl. ............................ 544/208; 204/72; 204/157
[58] Field of Search ........................ 204/157.72; 544/208

[56] References Cited

U.S. PATENT DOCUMENTS 3,637,688  1/1972  Rees et al. ............................ 260/249.9
5,712,277  1/1998  Nakamura et al. ..................... 514/242

*Primary Examiner*—James H. Reamer
*Attorney, Agent, or Firm*—Nixon & Vanderhye

[57] ABSTRACT

The invention provides a process for producing lamotrigine of formula (I):

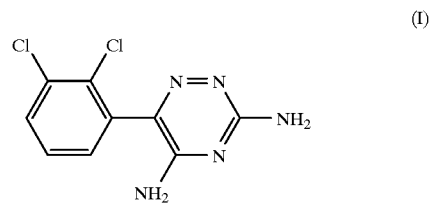

which process comprises subjecting a compound of formula (II):

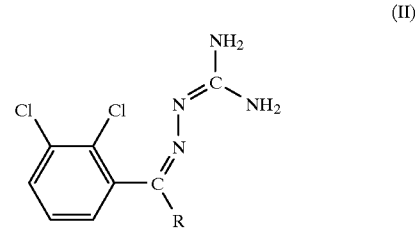

wherein R is CN or $CONH_2$, in an organic solvent, to ultra violet or visible radiation and, when R is CN, to heat.

7 Claims, No Drawings

PROCESS FOR THE PREPARATION OF LAMOTRIGINE

The present invention relates to a process for producing lamotrigine and its pharmaceutically acceptable acid addition salts.

Lamotrigine is 3,5-diamino-6-(2,3-dichlorophenyl)-1,2,4-triazine, of formula (I)

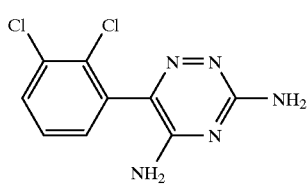
(I)

It is a known compound, useful in the treatment of disorders of the central nervous system (CNS), in particular epilepsy, described for example in EP-A-0021121. Lamotrigine isethionate, disclosed in EP-A-0247892, is a preferred salt for parenteral administration.

The present invention provides a process for producing lamotrigine, which process comprises subjecting a compound of formula (II:

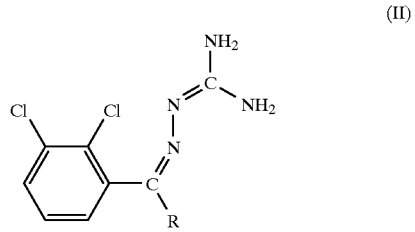
(II)

wherein R is CN or $CONH_2$, in an organic solvent, to ultra violet or visible radiation and, when R is CN, to heat.

Any organic solvent may be used in which the compound of formula (II) is soluble. A preferred example is a $C_1$–$C_6$ alkanol.

A $C_1$–$C_6$ alkanol may be a straight or branched-chain alkanol. It is, for instance, a $C_1$–$C_4$ alkanol, for example methanol, ethanol, n-propanol, i-propanol, n-butanol, s-butanol, or t-butanol, or a mixture thereof.

When R in formula (II) is CN, the process of the invention requires the application of heat to the compound of formula (II). In that case the process is preferably conducted by irradiating and heating the compound of formula (II) in the solvent. The solution may, for instance, be heated on a steam bath. It is suitably heated to the reflux temperature of the organic solvent. The solution may first be irradiated at ambient temperature and then subsequently heated, for example to reflux. Alternatively the solution may first be heated, for example to reflux, and then subsequently irradiated. The solution is suitably maintained at or near reflux temperature whilst irradiation takes place. For instance, the solution may be heated to reflux and then circulated through a falling film photochemical reactor in which it is exposed to radiation of a suitable intensity and duration.

When R in formula (II) is $CONH_2$ the process of the invention does not necessarily require heat. In that case the solution of the compound of formula (II) in an organic solvent may be irradiated at ambient temperature, for instance at a temperature of from 18° C. to 25° C., or from 20° C. to 25° C., preferably at 25° C. However, the solution may optionally be heated before, during or after irradiation, for instance as described above for compounds of formula (II) wherein R is CN.

Irradiation of a compound of formula (II) in the organic solvent may suitably be performed by exposure to sunlight, to a tungsten lamp, to a fluorescent lamp or to a medium pressure Hg lamp. Irradiation may also be performed by exposure to both sunlight and a tungsten lamp, or to both sunlight and a medium pressure lamp. A tungsten lamp is suitably a 150W lamp.

Irradiation is continued for a sufficient period of time to effect cyclisation of the compound of formula (II) to lamotrigine. The amount of time which is appropriate will depend inter alia on the source or sources of radiation, on the intensity of radiation, on the nature of the reaction vessel and on the temperature and pH of the solution being irradiated. Irradiation may, for instance, be continued for a period of from 2 hours to 5 days, for instance 2 hours to 4 days, or 2 hours to 2 days, or 2 hours to 1 day; or from 4 hours to 4 days, for instance 4 hours to 4 days, or 4 hours to 2 days, or 4 hours to 1 day; or from 2 hours to 24 hours, for instance 2 hours to 0 hours, or 2 hours to 18 hours; or from 4 hours to 24 hours for instance 4 hours to 20 hours, or 4 hours to 18 hours.

When R in formula (II) is $CONH_2$ the process of the invention is suitably carried out in the presence of a base. Any suitable base may be used, for example an alkali metal hydroxide such as potassium hydroxide or sodium hydroxide. Potassium hydroxide is especially preferred. The alkaline pH created by the use of a base is thought to promote the cyclisation of the compound of formula (II) to lamotrigine in favour of potentially competing photochemical processes. An example of such a competing process is E/Z isomerisation of the compound of formula (II), the product of which is a mixture of the compound of formula (II) and its Z-isomer, the compound of formula (III):

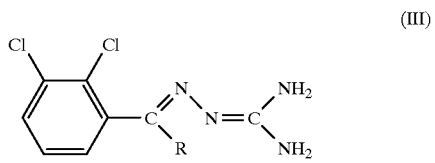
(III)

wherein R is CN or $CONH_2$

The conversion of the compound of formula (II) to lamotrigine is thought to occur by photochemical isomerisation to the Z-isomer of formula (III), which is not however isolated, followed by cyclisation of the Z-isomer to lamotrigine itself.

When R in formula (II) is $CONH_2$ another photochemical process may, under certain reaction conditions, compete with cyclisation to lamotrigine. This process is the conversion of the compound to 3-amino-5-hydroxy-6-(2,3-dichlorophenyl)-1,2,4-triazine of formula (IV):

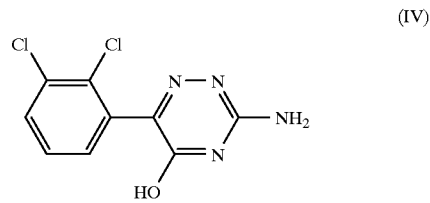
(IV)

As indicated above, the temperature and pH at which the process of the invention takes place can be influential in determining the course of the reaction. For instance, irradiation of a solution of compound II wherein R is $CONH_2$ in ethanol at neutral pH for 18 hours at 80° C. gives the hydroxy compound (IV) as defined above as the major cyclised product, with lamotrigine forming in a smaller amount. In contrast, heating a solution of compound II wherein R is $CONH_2$ in ethanol at an alkaline pH, for instance in the presence of KOH, followed by irradiation for about 3 hours, affords lamotrigine to the virtual exclusion of the hydroxy compound of formula (IV).

The compound of formula (II) wherein R is CN may be prepared by dehydrating the aminoguanidone oxime of formula (V)

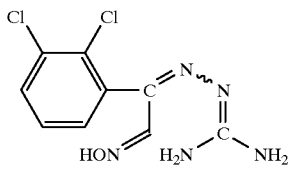

(V)

The reaction is preferably carried out by treating the compound of formula (V) with a suitable dehydrating agent, e.g. thionyl chloride, in a suitable organic solvent, e.g. dimethylformamide. It was found that dehydration of a mixture of the (E)- and (Z)-isomers of the compound of formula (V) afforded substantially only the (E)-isomer of the compound of formula (II).

The compound of formula (V) is novel. The invention therefore further provides a compound of formula (V) as defined above. The compound of formula (V) may be prepared by treating 2,3-dichlorophenylglyoxal aldoxime of formula (VI)

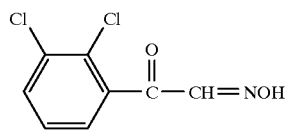

(VI)

with aminoguanidine or a salt thereof. The reaction is preferably performed in a suitable solvent, such as dimethyl sulphoxide or dimethyl formamide, in the presence of an acid. Typically the acid is concentrated hydrochloric acid, for instance 8N hydrochloric acid. The reaction may be conducted at ambient temperature.

The compound of formula (VI) may be prepared by nitrosating 2,3-dichloroacetophenone of formula (VII)

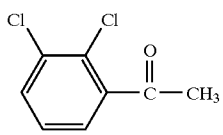

(VII)

with a suitable nitrosatiny agent, preferably a $C_{1-6}$ alkyl nitrite or nitrous acid, more preferably amyl nitrite. The reaction is preferably carried out in the presence of an acid or base catalyst in a suitable organic solvent, e.g. an ether or alcohol, preferably diethyl ether or t-butanol, at a temperature ranging from about 15° C. to the boiling point of the solvent. The acid catalyst when used is preferably hydrogen chloride. The base catalyst when used is preferably potassium t-butoxide. The reaction may be performed at room temperature.

The compound of formula (VII) may be prepared by treating 1,2-dichlorobenzene with a compound of formula $RM^1$ or $RM^2X$, wherein R represent $C_{1-6}$ alkyl, $M^1$ represents an alkali metal, $M^2$ represents an alkaline earth metal and X represents halogen, followed by the reaction of the compound thus obtained with acetyl chloride or acetic anhydride. $RM^2X$ may, for example, represent a Grignard reagent such as methylmagnesium iodide. A compound of formula $RM^1$ is preferably used, butyl lithium being especially preferred. followed by reaction with acetic anhydride. The reaction is preferably performed at a temperature of about −70° C.

The compound of formula (VII) may also be prepared by treating 2,3-dichlorobenzaldehyde with a compound $RM^1$ or $RM^2X$ wherein R is methyl, preferably with methylmagnesium iodide, and oxidising the α-methyl-2,3-dichlorobenzyl alcohol thus obtained. Suitable oxidising agents include, for example, sodium hypochlorite. The reaction is preferably performed at room temperature.

The compound of formula (VII) may also be prepared by treating 2,3-dichloroiodobenzene with magnesium and reacting the compound thus obtained with acetyl chloride in the presence of anhydrous ferric chloride. The reaction is preferably performed at a temperature of about −70° C.

The compound of formula (II) wherein R is CN may alternatively be prepared by dehydrating the corresponding amide, which is the compound of formula (II) wherein R is $CONH_2$. Conventional dehydrating agents may be used, for example pyrophosphoryl chloride.

The starting compound of formula (II) wherein R is $CONH_2$ is prepared by a process which comprises treating 2,3-dichlorophenylglyoxylamide of formula (VIII):

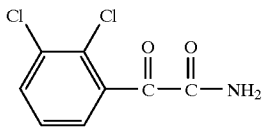

(VIII)

with aminoguanidine or a salt thereof.

When a salt of aminoguanidine is used it is preferably aminoguanidine hydrochloride.

The reaction of the compound of formula (VIII) with aminoguanidine or its salt is preferably carried out in a suitable organic solvent such as a $C_1-C_6$ alkanol, for instance ethanol, in the presence of an acid at an elevated temperature. The acid is typically a concentrated acid, for instance concentrated hydrochloric acid. The reaction is suitably performed at the reflux temperature of the organic solvent which is used.

The compound of formula (VIII) is novel. The invention therefore further provides a compound of formula (V) as defined above.

The compound of formula (VIII) may be prepared by treating 1,2-dichlorobenzene with a compound of formula $RM^1$ or $RM^2X$, wherein R represents $C_{1-6}$ alkyl, $M^1$ represents an alkali metal, $M^2$ represents an alkaline earth metal and X represents halogen, followed by reaction of the compound thus obtained with a $C_{1-6}$ alkyl oxamate. $RM^2X$ may, for example, represent a Grignard reagent such as methylmagnesium iodide. A compound of formula $RM^1$ is preferably used, n-butyl lithium being especially preferred. The alkyl oxamate is preferably ethyl oxamate.

The reaction is preferably carried out by treating a solution of 1,2-dichlorobenzene in a suitable organic solvent, e.g. an ether such as diethyl ether, dioxane or tetrahydrofuran, with a solution of n-butyl lithium in a suitable organic solvent, e.g. hexane, at a temperature preferably below about −60° C. n-Butyl lithium may be formed in situ by reacting n-butyl chloride with lithium.

The compound of formula (VIII) may also be prepared by activating 2,3-dichlorophenyl glyoxylic acid by conversion to the corresponding and anhydride or acid halide, and then treating the activated derivative with ammonia. Alternatively, the ammonium salt of 2,3-dichloropheny glyoxylic acid may be dehydrates to give the compound of formula (VIII). Such methods are conventional for the conversion of acids to amides and are routine in organic synthesis.

The compound of formula (VIII) may also be prepared by treating ethyl 2,3-dichlorophenylglyoxylate of formula (IX):

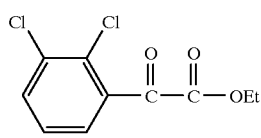

(IX)

with ammonia. The reaction is preferably performed in a suitable solvent, e.g. a $C_{1-6}$ alkanol such as methanol, ethanol, propan-1-ol or propan-2-ol, preferably methanol.

Ethyl 2,3-dichlorophenylglyoxylate is novel. The invention therefore further provides the compound of formula (IX) as defined above.

The compound of formula (IX) is preferably prepared by treating 1,2-dichlorobenzene with a compound of formula $RM^1$ or $RM^2X$, wherein R represents $C_{1-6}$ alkyl, $M^1$ represents an alkali metal, $M^2$ represents an alkaline earth metal and X represents halogen, followed by the reaction of the compound thus obtained with an ethyloxalyl halide, for example ethyloxalyl chloride. $RM^2X$ may, for example, represent a Grignard reagent such as methylmagnesium iodide. A compound of formula $RM^1$ is preferably used, n-butyl lithium being especially preferred.

The invention also provides a process which further comprises forming a pharmaceutically acceptable acid addition salt of lamotrigine.

Suitable pharmaceutically acceptable acid addition salts of lamotrigine include the sulphate, phosphate, methanesulphonate, p-toluenesulphonate, benzenesulphonate and isethionate salts. Lamotrigine isethionate is particularly preferred for parenteral administration as it has a high solubility in water.

Lamotrigine isethionate may be prepared by reacting lamotrigine with isethionic acid. Preferably the molar ratio of lamotrigine to isethionic acid is from 1:3 to 3:1, and in particular approximately 1:1.

Isethionic acid is not commercially available and is therefore conveniently made in situ. For example an alkali metal isethionate in solution may be converted to isethionic acid e.g. by passing an aqueous solution of the isethionate through an $H^+$ ion-exchange resin, and the triazine is then mixed with the resulting acid solution. Typically the reaction solvent is water and when this is so the reaction may be performed at temperatures of from 4 to 50° C., conveniently at ambient temperature and without the need for any pH adjusters or other additives.

The isethionate salt formed may be recrystallized from e.g. industrial methylated spirit to produce crystals of lamotrigine isethionate which readily dissolve in water.

Alternatively, lamotrigine isethionate may be prepared by reacting a lamotrigine salt other than isethionate with isethionate anion. Preferably the ratio of salt to anion is from 1:50 to 50:1. More preferably the ratio is approximately 1:10. Preferably the reaction is carried out by eluting a solution of the salt in methanol through a column of isethionate anion exchange resin. In this case the salt is preferably lamotrigine methanesulphonate (mesylate).

The invention also provides a process further comprising the preparation of a pharmaceutical composition by formulating lamotrigine or a pharmaceutically acceptable acid addition salt thereof with a pharmaceutically acceptable diluent or carrier.

Lamotrigine will be present in the compositions prepared according to the invention in an effective unit dosage form, i.e. in an amount sufficient to be effective against CNS disorders in vivo.

The pharmaceutically acceptable diluent or carrier present in the compositions prepared according to the invention may be a liquid or solid material which is inert or medically acceptable and which is compatible with lamotrigine or its salt.

The pharmaceutical compositions may be given orally or parenterally, used as a suppository, or applied topically as an ointment, cream or powder. However, oral or parenteral administration of the composition is preferred.

For oral administration, fine powders or granules may be used which contain diluting, dispersing and/or surface active agents, and which may be presented in a draught, in water or in a syrup, in capsules or sachets in the dry state or in non-aqueous suspension wherein suspending agents may be included, or in a suspension in water or syrup. Where desirable or necessary, flavouring, preserving, suspending, thickening or emulsifying agents may be included. When a suspension is prepared in water according to the present invention at least one of these agents is preferably present.

For parenteral administration, the active compound may be presented in a sterile aqueous injection solution which may contain anti-oxidants or buffers.

Lamotrigine or a salt thereof may be administered in pure form unassociated with other additives in which case a capsule or sachet is the preferred carrier.

Alternatively the active compound may be presented in pure form as an effective unit dosage, e.g. compressed as a tablet or the like.

Other materials which may be included are, for example, medically inert ingredients, e.g. solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets and other forms of presentation provided in discrete units may conveniently contain an amount of lamotrigine or a salt thereof which is effective at that dosage or at a multiple of that dosage, e.g. units containing 5 mg to 500 mg, preferably around 10 mg to 250 mg, calculated as the free base.

Aqueous formulations will generally comprise a pharmaceutically acceptable salt of lamotrigine in an amount sufficient to be effective against CNS disorders in vivo and the formulation may be in unit dosage form. Up to about 250 mg/ml of the salt, calculated as free base, may be present in aqueous formulation. However, typical concentrations of the salt in solution are 10 to 70 mg/ml, preferably 10 to 50 mg/ml. For parenteral administration the salt may be presented in sterile aqueous injection solutions which may contain therapeutically acceptable accessory ingredients such as antioxidants, buffers and agents to adjust the osmolarity of the solution. Preferably anions such as chloride and phosphates are not present in the solution, since these tend to exchange with the salt to form precipitates.

An aqueous formulation may be prepared by dissolving the salt in aqueous media, suitably sterile water for injection. The solution may be diluted before use to the required concentration.

The following Examples illustrate steps of the process of the invention.

REFERENCE EXAMPLE 1

Preparation of (E)-2-(2',3'-Dichlorophenyl)-2-(guanidinylimino) acetamide (Compound (II)) with R=CONH$_2$)

A mixture of 2,3,-dichlorophenylglyoxylamide (54.5 g, 0.25 mol), aminoguanidine hydrochloride (33.15 g, 0.30 mol), ethanol (1 liter) and concentrated hydrochloric acid (4ml) were heated under reflux for 6 hours (pH≈1.5). The resulting solution was evaporated to dryness, the solid was dissolved in water (2 liters; resulting pH=2.5) and the solution was basified to pH 13 by the addition of 50% w/v aqueous sodium hydroxide (45 ml) at <15°. The mixture was filtered, the buff solid washed with 0.88 ammonia solution and dried to give the crude product (59.5 g, 87%) m.p. 231–3° (ref. 233–4° decomp.). Recrystallisation of this product (2.2 g) from propan-1-ol (60 ml) afforded pure material (1.83 g, 83%) m.p. 238–9° (decomp.).

REFERENCE EXAMPLE 2

Preparation of (E)-2-(2,3-dichlorophenyl)-2-(quanidinylimino) acetonitrile (Compound (II) with R=CN)

The aminoguanidone oxime of formula (V) defined above was dissolved in dimethylformamide and treated with thionyl chloride. A crude product was obtained which contained several minor impurities. The impurities were readily removed by trituration with toluene to afford (E)-2-(2,3-dichlorophenyl)-2-guanidinyliminoacetonitrile in 24% yield.

EXAMPLE 1

Preparation of Lamotrigine (E)-2-(2',3'-dichlorophenyl)-2-(guanidinylimino) acetamide as described in Reference Example 1 (0.3 g) was dissolved in ethanol (10 ml) and was irradiated by exposure to sunlight.

TLC after 4 hours of irradiation showed that a mixture of compound (II) and its Z isomer, compound (III), was present in the solution, but that no lamotrigine had formed. After 2 days, however, TLC revealed a spot corresponding to lamotrigine (Rf=0.20). A baseline spot for an unidentified material was also detected. TLC analysis of the solution after a total of 4 days showed that lamotrigine was still present.

A suspended solid which had formed at the pump was then filtered and found to give a TLC spot near the baseline. Lamotrigine was detected by TLC in the remaining liquor. Irradiation of a sample of the liquor was therefore continued for one day. A strong spot for lamotrigine was detected by TLC. Melting point of lamotrigine=218° C.

EXAMPLE 2

Preparation of Lamotrigine (E)-2-(2',3'-dichlorophenyl)-2-(guanidinylimino) acetamide (2.5 g) was dissolved in hot ethanol (40 ml). Potassium hydroxide (2.0 g, equivalent to 5% w/v) was added and the solution was irradiated by exposure to bright sunlight and a tungsten lamp (15W).

After 4 days of irradiation with the lamp a medium intensity spot corresponding to lamotrigine was revealed by TLC (Rf=0.20).

The basic ethanolic solution was therefore acidified to pH 6 with concentrated hydrochloric acid (3 ml). Silica gel (2.0 g) was added and the whole was evaporated to dryness. The resulting fine white powder was loaded onto a silica gel column and eluted as follows:

| a) | 10% MeOH in CHCl$_3$ | Fraction | 1 | 200 ml (main solvent) |
|----|----------------------|----------|---|------------------------|
|    |                      |          | 2 | 100 ml clear |
|    |                      | brown oil | 3 | 100 ml pale yellow |
| b) | 20% MeOH in CHCl$_3$ | brown oil | 4 | 100 ml very pale yellow |
|    |                      | yellow oil | 5 | 100 ml clear |
| C) | 30% MeOH in CHCl$_3$ | white solid | 6 | 100 ml clear |
|    |                      |          | 7 | 100 ml clear |

(*contained fluorescent impurities)

The white solid was identified as lamotrigine by TLC. This was confirmed by mass spectroscopy and melting point measurement (m.pt=218° C.).

EXAMPLE 3

Preparation of Lamotrigine (E)-2-(2',3'-dichlorophenyl)-2-(guanidinylimino) acetamide (2.0 g) was dissolved in a solution of potassium hydroxide (5% w/v) in ethanol (40 ml). The solution was irradiated at ambient temperature using a medium pressure lamp for a total of 12 hours. The solution was left to stand, and then heated on a steam bath at 70° C. for 2 hours.

TLC analysis of the solution after 4 hours revealed the presence of a trace amount of lamotrigine (Rf=0.20) together with a 50:50 mixture of compound II and its Z isomer, compound III. TLC of the solution was repeated after a total of 6.5 hours, 9 hours and 12 hours. Each time the plate showed a faint spot corresponding to lamotrigine with a stronger spot corresponding to the E/Z mixture of compounds II and III. These results suggested that whilst E/Z isomerisation of compound II occurred very rapidly, cyclisation of compound II to lamotrigine, under the reaction conditions employed, was slow.

EXAMPLE 4

Preparation of Lamotrigine

Method

A solution of (E)-2-(2',3'-dichlorophenyl)-2-(guanidinylimino)acetamide (2.2 g) in ethanol (100 ml) was heated to reflux and circulated through the falling film photochemical reactor. The solution was analysed by TLC at intervals (2½ hours, 5 hours, 7½ hours, 10 hours, 13 hours) throughout the course of the reaction. When the reaction has continued for 10 hours the solution was a deep yellow colour. After a total of 13 hours the solution was orange and a white solid had begun to precipitate out. The reaction was then stopped. The white solid was filtered off and examined by TLC.

Result

At 2½ hours, TLC of the solution showed that lamotrigine was beginning to form. Unreacted compound II was also present. After 5 hours unreacted compound II and lamotrigine were still present, but an additional spot with a higher Rf value was detected. At each 7½, 10 and 13 hours the same observation was made.

The white solid was identified by TLC as a pure sample of 3-amino-5-hydroxy-6-(2,3-dichlorophenyl)-1,2,4-triazine.

EXAMPLE 5

Preparation of Lamotrigine (E)-2-(2',3'-dichlorophenyl)-2-guanidinylimino) acetamide (5.0 g) was dissolved in hot ethanol (150 ml) containing potassium hydroxide (2% w/v). The resulting yellow solution was irradiated at 25° C. using a medium pressure lamp. TLC analysis of the solution after irradiation for 3 hours and 5 hours, respectively, showed that lamotrigine had not formed in a detectable amount.

The solution was therefore heated to reflux and then irradiated using a medium pressure lamp. After 3 hours or irradiation TLC analysis showed that lamotrigine was present. No 3-amino-5-hydroxy-6-(2,3-dichlorophenyl)-1,2,4-triazine was detected.

Recrystallisation from ethanol containing 5 g charcoal afforded 3,5-diamino-6-(2,3-dichlorophenyl)-1,2,4-triazine.EtOH (31 g, 56%) as a very pale yellow solid m.p. 219–220° C. (ref. 220–222° C.). T.l.c. using silica gel/ethyl acetate revealed a trace amount of a fluorescent baseline impurity.

EXAMPLE 6

Preparation of Lamotrigine (E)-2-(2,3-dichlorophenyl)-2-guanidinylimino-acetonitrile as described in Reference Example 2 was dissolved in propan-1-ol and irradiated at reflux as shown in the table below. Evaporation of the resulting solution and recrystallisation of the solid residue from ethanol afforded colourless, homogeneous 3,5-diamino-6-(2,3-dichlorophenyl)-1,2,4-triazine.EtOH in all but the final case.

4-triazine.EtOH (31 g, 56%) as a very pale yellow solid m.p. 219–220° C. (ref. 220–222° C.). T.l.c. using silica gel/ethyl acetate revealed a trace amount of a fluorescent baseline impurity.

EXAMPLE 7

Preparation of the Aminoguanidone Oxime of Formula (V)

2,3-Dichlorophenylglyoxal aldoxime was condensed with aminoguanidine in a mixture of dimethylsulphoxide and 8N hydrochloric acid at ambient temperature. The reaction mixture was basified with concentrated ammonium hydroxide solution and the aminoguanidone oxime was isolated in 73% yield as an equimolar mixture of (E)- and (Z)-isomers.

REFERENCE EXAMPLE 3

Preparation of 2,3-dichlorophenylglyoxal Aldoxime of Formula (VI)

Method A 2,3-Dichloroacetophenone (20.00 g, 0.104 mol) was dissolved in dry diethyl ether (200 ml) and hydrogen chloride bubbled through the solution for half an hour. Amyl nitrite (24.36 g, 0.238 mol) was added dropwise, with stirring, so that the solution was maintained at a gentle reflux. The solution was then gently refluxed for 3 hours with continued passage of hydrogen chloride. The solution was allowed to stand at room temperature overnight. The reaction mixture was poured into 2N sodium hydroxide solution (200 ml) with extreme caution (very vigorous reaction), and separated. The organic phase was extracted with 2N sodium hydroxide solution (2×100 ml). The alkaline phases were combined, poured onto ice (200 ml) and Concentrated hydrochloric acid (100 ml) added with stirring. The resulting acid mixture was allowed to stand at room temperature overnight and the precipitate which formed was filtered at the pump. 2,3-Dichlorophenylglyoxal aldoxime was afforded as a cream solid (10.4 g, 46% yield). T.l.c. (SiO$_2$CHCl$_3$) showed no impurities, therefore no further purification was attempted.

Method B

Potassium t-butoxide (239.7 g, 2.136 mol) was dissolved in t-butanol (1.5 liters) and allowed to stir at room tempera-

| Wt. of nitrile | Vol. of propanol | Radiation source | Reaction time | % Yield of lamotrigine.EtOH |
|---|---|---|---|---|
| 0.1 g | 8 ml | 150 W Tungsten lamp | 24 hr | 60 |
| 0.1 g | 8 ml | 8 W fluorescent lamp | 24 hr | mainly lamotrigine.EtOH |
| 0.1 g | 2 ml | Medium Pressure Hg lamp | 3 hr | 51 |
| 3.0 g | 30 ml | " | 8 hr | 73 |
| 47.0 g | 470 ml | " | 32 hr | 57 (yellow) |

In the small-scale experiments the conversion to 3,5-diamino-6-(2,3-dichlorophenyl)-1,2,4-triazine was very clean (t.l.c.) and the low yields reflect losses on handling. In the final 47 g experiment, conversion to 3,5-diamino-6-(2,3-dichlorophenyl)-1,2,4-triazine was approximately 50% complete after 8 hrs, but after 32 hrs a yellow cloudy reaction mixture resulted. This was filtered, evaporated to low volume, cooled and filtered to give crude 3,5-diamino-6-(2,3-dichlorophenyl)-1,2,4-triazine (32.2 g, 68%) as a pale yellow solid. Recrystallisation from ethanol containing 5 g charcoal afforded 3,5-diamino-6-(2,3-dichlorophenyl)-1,2, ture for 30 minutes. 2,3-Dichloroacetophenone (67.26 g, 0.356 mol) was added in one portion and the resulting mixture stirred overnight at room temperature. Amyl nitrite (83.41 g, 0.712 mol) was added slowly dropwise, with stirring. When the addition was complete the reaction mixture was stirred at room temperature for 2 hours and then heated at 50° C. for 2 hours. The solution was allowed to cool and stirred at room temperature overnight. The reaction mixture was poured into ice/water (1.5 liters), and the aqueous solution extracted with diethyl ether (3×500 ml). The aqueous phase was acidified with concentrated hydrochloric acid and allowed to stand at room temperature overnight. The solid which precipitated was filtered at the pump and dried under vacuum over anhydrous phosphorus pentoxide to give 2,3-dichlorophenylglyoxal aldoxime (57.3 g, 73.8%) as a brown solid. T.l.c. (SiO$_2$; CHCl$_3$) showed little impurity, but subsequent dehydration of the oxime showed that recrystallisation would be advisable. The oxime may be recrystallised from toluene, m.p. 109° C.

REFERENCE EXAMPLE 4

Preparation of 2,3-dichloroacetophenone

Method A

Butyl lithium in hexane (300 ml, 0.474 mol) was added slowly dropwise, with stirring, to 1,2-dichlorobenzene (104.58 g, 0.711 mol) dissolved in dry tetrahydrofuran (2 liters) maintained at a temperature of −70° C., under nitrogen. The resulting solution was stirred at −70° C. for 1 hour. This solution, still at −70° C., was added to acetic anhydride (290.35 g, 2.84 mol), dissolved in dry tetrahydrofuran (1 liter) at −70° C., under nitrogen via a double ended needle. When addition was complete the resulting solution was stirred at −70° C. for approximately 1 hour and allowed to come to room temperature.

The reaction mixture was poured onto ice (5 liters) and after stirring well was allowed to stand overnight at room temperature. The aqueous mixture was extracted with ether (3×1.5 liters). The ether phases were combined, washed with water (3×750 ml), saturated sodium bicarbonate solution (3×750 ml), and brine (1×750 ml). The organic phase was dried over anhydrous magnesium sulphate, filtered and evaporated, to give a yellow liquid. The crude product was put under high vacuum in a hot water bath, in order to remove any 1,2-dichlorobenzene and acetic anhydride. 2,3-Dichloroacetophenone (67.2 g, 75% yield) was obtained. Ir, nmr and t.l.c. (SiO$_2$;CHCl$_3$) showed the material to contain few impurities, therefore no further purification was attempted.

Method B

Iodomethane (324.89 g, 2.288 mol) was added dropwise, with stirring, to magnesium turnings (54.88 g, 2.288 mol) in dry ether (1 liter), to form methyl-magnesium iodide. 2,3-Dichlorobenzaldehyde (200 g, 1.144 mol) dissolved in benzene/diethyl ether (1 liter, 50:50) solution was added dropwise, with stirring, to the Grignard. The reaction mixture was allowed to stir at room temperature overnight. The solution was refluxed for 2 hours, and then allowed to cool. The reaction mixture was poured into saturated ammonium chloride solution (5 liters) and the organic layer separated. The aqueous layer was extracted with ether (3×2 liters). The organic phases were combined, washed with brine (1×2 liters), dried over anhydrous magnesium sulphate, filtered and evaporated down. α-Methyl-2,3-dichlorobenzyl alcohol (196.4 g, 90% yield) was obtained as a yellow oil which crystallised on standing to give a pale-yellow solid. T.l.c. (SiO$_2$;CHCl$_3$) showed no impurities so no further purification was carried out. However, if necessary the alcohol may be recrystallised from 40–60° C. petroleum ether to afford white prisms of melting point 53° C.

α-Methyl-2,3-dichlorobenzyl alcohol (5.0 g, 0.026 mol was dissolved in acetic acid (24 ml) and 12% w/v sodium hypochlorite solution (23.26 ml, 0.0314 mol) was added slowly dropwise, with stirring, at a temperature of 15–25° C. When the addition was complete the reaction mixture was stirred at ambient temperature for approximately 1½ hours until a starch/iodide test gave a positive result. Saturated sodium bisulphite solution was added to the reaction mixture until the starch/iodide test was negative. The mixture was poured onto ice/brine (100 ml) and extracted with diethyl ether (3×75 ml). The ether phases were combined and washed with 2N sodium hydroxide solution (3×75 ml) until the aqueous washes were alkaline. The ether phase was dried over anhydrous magnesium sulphate, filtered and evaporated down. 2,3-Dichloroacetophenone (3.2 g, 65% yield) was afforded as a pale-yellow oil. T.l.c. (SiO$_2$;CHCl$_3$) and nmr showed this material to contain no impurities.

Method C 2,3-Dichloroiodobenzene (350 g, 1.282 mol) dissolved in dry ether (1250 ml) was added slowly, with stirring, to magnesium turnings (30.77 g, 1.282 mol) in dry diethyl ether (300 ml), in order to form 2,3-dichlorophenylmagnesium iodide under nitrogen. The Grignard was added dropwise, with stirring, to acetyl chloride (301.91 g, 3.846 mol) dissolved in dry diethyl ether (1 liter) and anhydrous ferric chloride (1.925 g, 0.0118 mol) at a temperature of −70° C. under nitrogen. When addition was complete the resulting mixture was stirred at −70° C. for a further 5 minutes, and then allowed to come to room temperature. The reaction mixture was poured onto ice (5 liters) and stirred thoroughly. The aqueous mixture was basified with sodium carbonate and allowed to stand at room temperature overnight. The aqueous solution was extracted with diethyl ether (3×2 liters) and the ether phases combined, dried over anhydrous magnesium sulphate, filtered, and evaporated down. Crude 2,3-dichloroacetophenone (235.7 g) was obtained as a yellow liquid. The crude material was distilled under vacuum to yield pure 2,3-dichloroacetophenone (147.0 g, b.p. 100° C./2 mmHg; 60.66% yield). Nmr and t.l.c. (SiO$_2$;CHCl$_3$) showed the distilled product to contain no impurities.

EXAMPLE 8

Preparation of 2,3-dichlorophenylglyoxylamide (Compound VIII)

1. Rapid laboratory procedure

A stirred solution of 1,2-dichlorobenzene (50.0 g, 0.34 mol) in dried tetrahydrofuran (500 ml) was cooled to −65° C. under N$_2$ and treated dropwise over 1 hour with a solution of n-butyl lithium in hexane (204 ml of 1.72 molar=0.35 mol), with the temperature held below −60° C. After stirring for a further 1 hour the pale yellow solution was treated dropwise with a solution of ethyl oxamate (19.9 g, 0.17 mol) in warm tetrahydrofuran (200 ml) with the reaction temperature held below −60° C. During this addition the reaction mixture changed from yellow through orange to Burgundy red. After stirring for a further 1 hour at −60° C. the mixture was allowed to warm to 0° C. over 2 hours, treated cautiously with water (250 ml) and acidified to pH 6 with hydrochloric acid. The yellow organic phase was separated, washed with brine (2×250 ml), dried (magnesium sulphate) and evaporated to give a yellow solid. This was slurried with ethanol (300 ml) and filtered to give crude 2,3-dichlorophenylglyoxylamide (12.0 g, 32.4%) as an off-white solid m.p. 213–214° C. (ref. m.p. 216–218° C.). Concentration of the ethanolic filtrate to 150 ml afforded a second crop (7.0 g, 18.9%) m.p. 205–206° C.

In a different experiment, crude 2,3-dichlorophenylglyoxylamide (40 g, m.p. 199–203° C.) was recrystallised from acetic acid (240 ml) and water (180 ml) affording 33.4 g (83%) of purified material (m.p. 216–218° C.).

The 2,3-dichlorophenylglyoxylamide was characterised as follows:
Molecular wt: 217.9
Melting pt: 216–218° C.

| Microanalysis: | C | H | N |
|---|---|---|---|
| Calc | 44.07 | 2.31 | 6.42 |
| Found | 44.79 | 2.63 | 6.09 |

2. In situ generation of butyl lithium n-Butyl chloride (55.5 g, 0.6 mol) was added dropwise to a stirred suspension of lithium slices (8.30 g, 1.2 mol) in dried ether (300 ml) under $N_2$ so as to maintain gentle reflux. After heating under reflux for a further 3¾ hours the mixture was cooled to room temperature and stirred overnight. (Previous analyses indicate that this procedure affords a 66% yield of butyl lithium (≡0.4 mol). The mixture was then cooled to −60° C. and held at this temperature during the following operations. Dried tetrahydrofuran (400 ml) was added, then a solution of 1,2-dichlorobenzene (58.8 g, 0.4 mol) in dried tetrahydrofuran (300 ml) was added dropwise over 40 mins. After stirring the mixture for 1 hour a solution of ethyl oxamate 23.4 g, 0.2 mol) in warm tetrahydrofuran (300 ml) was added dropwise over 1 hour and the mixture stirred for a further 1 hour at −60° C. After allowing to warm to 0° C., water (300 ml) was added cautiously and the mixture acidified to pH 6 within hydrochloric acid. The yellow organic phase was separated, washed with brine (2×300 ml), dried (magnesium sulphate) and evaporated to give a pale yellow solid. This was slurried with ethanol (250 ml), filtered and dried to give crude 2,3-dichlorophenylglyoxylamide (22.5 g, 52%) m.p. 214–215° C. (ref. 215–218° C.).

EXAMPLE 9

Preparation of Ethyl 2,3-dichlorophenylglyoxylate (Compound IX)

Materials
2,3-dichloroiodobenzene (0.1M, 27.3 g) in 35 ml dry ether
magnesium (2.43 g) in 15 ml dry ether
cadmium chloride (0.1M, 9.8 g)
ethyl oxalyl chloride (0.079M, 10.9 g, 8.92 ml)
reaction performed under nitrogen Method A Grignard reagent was prepared in conventional manner as follows:

The dichloroiodobenzene was added to magnesium over 1–2 hours and the resulting solution was refluxed for about 4 hours. As all the Mg had not dissolved the Grignard was allowed to stir at room temperature overnight.

The flask was then cooled in ice and the dry cadmium chloride added portionwise over 10 minutes. When all the cadmium chloride had been added the reaction mixture was allowed to warm to room temperature and was then heated under reflux for 45 minutes.

The ether was evaporated off and the residue washed twice with dry benzene which, in was turn, also evaporated off.

The residue was then taken and treated with ethyl oxalyl chloride in 20 mls dry benzene. This was added slowly from a dropping funnel with stirring. The reaction was very vigorous. When addition was complete and spontaneous reflux had subsided the reaction mixture was refluxed for a further hour.

The reaction mixture was then cooled in an ice bath. Ice/water was carefully added. Sufficient 20% $H_2SO_4$ was then added to give two clear phases. The aqueous phase was separated and extracted twice with benzene. The benzene layers were combined and extracted 1×water, 1×$Na_2CO_3$ solution, 1×water and 1×NaCl solution. The benzene solution was then dried over $MgSO_4$, filtered and evaporated down. 17.5 g crude material was obtained.

NMR and TLC analyses were performed. TLC in Si/$CHCl_3$ gave two spots, one corresponding to the title compound (product) and one to the dichloroiodobenzene (starting material).

EXAMPLE 10

Preparation of Ethyl 2.3-dichlorophenylglyoxylate (Compound (IX))

Materials
2,3-dichloroiodobenzene (0.2M, 54.6 g) in 150 ml ether
magnesium turnings (0.2M, 4.86 g) in 50 ml ether
cadmium chloride (0.2M, 19.6 g)
ethyl oxalyl chloride (0.15M, 21.8 g)
reaction performed under nitrogen Method The general method described in Example 7 was performed. However, the Grignard was not refluxed overnight as the reaction proceeded very rapidly due to the greater volume of ether.

On addition of ethyl oxalyl chloride the reaction mixture was cooled in ice and the resulting mixture stirred at room temperature overnight.

The reaction mixture was decomposed by the addition of ice/water, and sufficient 20% $H_2SO_4$ was added to give two separate layers.

The mixture was separated and the aqueous layers washed 2×benzene. The benzene layers were combined and washed with water. No alkaline wash was performed. The benzene layers were dried, filtered and evaporated down.

39.5 g of product was obtained. NMR and TLC gave identical analyses to those obtained in Example 9.

EXAMPLE 11

Preparation of 3,5-diamino-6-(2,3-dichlorophenyl)-1,2,4-triazine Isethionate

A solution of sodium isethionate (148 g, 1.0 mol) in water (4.9 liters) was passed down a column of IR 120 (H) ion-exchange resin and eluted with water. 3,5-Diamino-6-(2,3-dichlorophenyl)-1,2,4-triazine (256 g, 1.0 mol) was dissolved in the resulting isethionic acid, and the solution filtered and evaporated in vacuo. The residue was recrystallised from industrial methylated spirit to afford 3,5-diamino-6-(2,3-dichlorophenyl-1,2,4-triazine isethionate. Yield 273.3 g (72%), m.p. 242° C.

EXAMPLE 12

Preparation of 3,5-diamino-6-(2,3-dichlorophenyl)-1,2,4-triazine Isethionate 50 mmol of Amberlite (trade mark) IR-45 (OH) was mixed with 15 mmol (10 ml) aqueous isethionic acid and the resulting material was packed into a column. The column was then washed with methanol. 0.7 g (2 mmol) of a methanolic solution of 3,5-diamino-6-(2,3-dichlorophenyl)-1,2,4-triazine mesylate was eluted through the column. The elutant was evaporated in vacuo and the residue was recrystallised from industrial methylated spirit and gave 3,5-diamino-6-(2,3-dichlorophenyl)-1,2,4-triazine isethionate: Yield 300 mg (40%), m.p. 242–243° C.

EXAMPLE 13

74.625 g (0.195 mol) of 3,5-diamino-6-(2,3-dichlorophenyl)-1,2,4-triazine isethionate was added to and dissolved in around 900 ml of water for injections BP, and diluted to 1000 ml with further water for injections BP, to give an aqueous solution containing isethionate salt equivalent to 50 mg/ml of the 3,5-diamino-6-(2,3-dichlorophenyl)-1,2,4-triazine base. This solution was acceptable on tonicity grounds.

EXAMPLE 14

14.925 (0.039 mol) of 3,5-diamino-6-(2,3-dichlorophenyl)-1,2,4-triazine isethionate was added to a solution of 43.8 g (0.221 mol) of dextrose monohydrate in around 900 ml of water for injections BP and diluted to 1000 ml with further water for injections BP, to give an aqueous solution containing isethionate salt equivalent to 10 mg/ml of the 3,5-diamino-6-(2,3-dichlorophenyl)-1,2,4-triazine base. This solution was acceptable on tonicity grounds.

EXAMPLE 15

A pharmaceutical composition having the following ingredients was prepared.

| | |
|---|---|
| 3,5-Diamino-6-(2,3-dichlorophenyl)-1,2,4-triazine | 150 mg) |
| Lactose | 200 mg) |
| Maize Starch | 50 mg) |
| Polyvinylpyrrolidone | 4 mg) |
| Magnesium Stearate | 4 mg) |
| ) contents per tablet | |

The drug was mixed with the lactose and starch and granulated with a solution of the polyvinylpyrrolidone in water. The resultant granules were dried, mixed with magnesium stearate and compressed to give tablets of average weight 408 mg.

We claim:

1. A process for producing lamotrigine of formula (I):

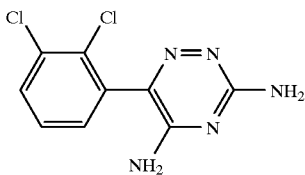

(I)

which process comprises subjecting a compound of formula (II):

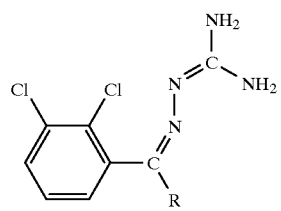

(II)

wherein R is CN or $CONH_2$, in an organic solvent, to ultra violet or visible radiation and, when R is CN, to heat to reflux temperature of the solvent, wherein period of irradiation or irradiation and heating is sufficient to effect cyclisation of the compound formula (II) to lamotrigine.

2. A process according to claim 1 wherein the compound of formula (II) is irradiated at reflux in propan-1-ol.

3. A process according to claim 1 wherein the compound of formula (II) wherein R is CN is prepared by dehydrating the compound of formula (V)

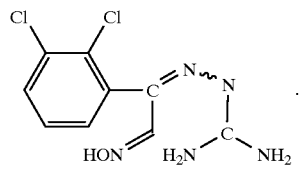

(V)

4. A process according to claim 1 wherein the compound of formula (II) wherein R is $CONH_2$ is prepared by treating 2,3-dichlorophenylglyoxylamide of formula (VIII):

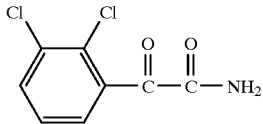

(VIII)

with aminoguanidine or a salt thereof.

5. A process according to claim 1 which further comprises converging lamotrigine into a pharmaceutically acceptable acid addition salt.

6. A process according to claim 5 wherein the salt is lamotrigine isethionate.

7. A process according to claim 1 which further comprises formulating lamotrigine or an acid addition salt thereof with a pharmaceutically acceptable carrier or diluent to produce a pharmaceutical composition.

* * * * *